US007641864B2

(12) United States Patent
Tremoulet, Jr. et al.

(10) Patent No.: US 7,641,864 B2
(45) Date of Patent: Jan. 5, 2010

(54) THERMAL SENSOR CONNECTOR FOR PRESSURE VESSEL

(75) Inventors: Olivier L. Tremoulet, Jr., Edmonds, WA (US); David O. Monserud, Seattle, WA (US); Edmund Y. Ting, Kent, WA (US)

(73) Assignee: Avure Technologies Incorporated, Kent, WA (US)

( * ) Notice: Subject to any disclaimer, the term of this patent is extended or adjusted under 35 U.S.C. 154(b) by 495 days.

(21) Appl. No.: 11/234,060

(22) Filed: Sep. 22, 2005

(65) Prior Publication Data

US 2006/0093531 A1 May 4, 2006

Related U.S. Application Data

(63) Continuation-in-part of application No. 09/883,091, filed on Jun. 15, 2001, now Pat. No. 7,220,381.

(51) Int. Cl.
*G05D 7/00* (2006.01)
*A61L 2/00* (2006.01)

(52) U.S. Cl. ................ 422/110; 422/111; 422/295; 73/865.9; 73/865.5; 374/141; 374/152

(58) Field of Classification Search ........... 73/865.9, 73/866.5; 374/141, 152; 422/110, 111, 295
See application file for complete search history.

(56) References Cited

U.S. PATENT DOCUMENTS

| | | | | |
|---|---|---|---|---|
| 4,203,943 A | * | 5/1980 | Gillis et al. | 422/27 |
| 4,416,417 A | | 11/1983 | Sanderson et al. | |
| 4,675,643 A | * | 6/1987 | Tanner et al. | 338/4 |
| 5,203,723 A | | 4/1993 | Ritter | |
| 5,528,941 A | * | 6/1996 | Ogawa | 73/756 |
| 5,587,601 A | * | 12/1996 | Kurtz | 257/417 |
| 5,639,255 A | | 6/1997 | Muzslay | |

(Continued)

FOREIGN PATENT DOCUMENTS

CA  2614685 A1  10/2000

(Continued)

OTHER PUBLICATIONS

International Search Report dated May 31, 2007.

*Primary Examiner*—N. Bhat
(74) *Attorney, Agent, or Firm*—Harness, Dickey & Pierce

(57) ABSTRACT

A connector for a pressure vessel includes a connector assembly having a first plurality of contacts, and a receiver assembly configured to be positioned within a receiver aperture formed in a closure of the pressure vessel and having a second plurality of contacts. The receiver assembly is configured to receive the connector assembly and place each of the first plurality of contacts in electrical contact with a corresponding one of the second plurality of contacts. A seal is provided between the connector assembly and the wall of the pressure vessel, for substantially sealing the receiver aperture from pressure within the vessel. The connector assembly is configured to be coupled to a product carrier, and sensors positioned in the vessel are coupled via the connector assembly to a data acquisition unit. When the closure is lowered onto the vessel, the receiver assembly contacts the connector assembly coupled to the carrier, closing the electrical contacts connecting the sensors to the acquisition unit.

6 Claims, 8 Drawing Sheets

U.S. PATENT DOCUMENTS

| | | | |
|---|---|---|---|
| 6,783,396 B1 | 8/2004 | Osterhart et al. | |
| 7,159,464 B2 * | 1/2007 | Tohyama et al. | 73/706 |
| 7,231,830 B2 * | 6/2007 | Otsuka et al. | 73/756 |
| 2002/0104673 A1 | 8/2002 | Miller et al. | |
| 2005/0087020 A1 * | 4/2005 | Ueyanagi et al. | 73/753 |

FOREIGN PATENT DOCUMENTS

| | | |
|---|---|---|
| EP | 1150392 | 10/2001 |
| GB | 2115238 | 9/1983 |
| JP | 06-007135 A | 1/1994 |
| WO | WO 2005/084281 | 9/2005 |

* cited by examiner

THERMAL SENSOR CONNECTOR FOR PRESSURE VESSEL

CROSS-REFERENCE TO RELATED APPLICATION

This application is a continuation-in-part of U.S. patent application Ser. No. 09/883,091, filed Jun. 15, 2001, now U.S. Pat. No. 7,220,381, which application is incorporated herein by reference in its entirety.

BACKGROUND OF THE INVENTION

1. Field of the Invention

Disclosed embodiments of the invention generally relate to pressure vessels for high pressure treatment processes, and more particularly, to temperature sensors and associated connectors positioned within such vessels.

2. Description of the Related Art

Pressure vessels are commonly used in various industries for manufacturing and product treatment. Typically, a pressure vessel includes a cylindrical body and upper and lower closures, which are used to close the ends of the cylindrical body. The product or device to be treated is placed within the pressure vessel, the vessel is filled with a pressure medium, and the interior of the vessel is subjected to extremely high pressures, generally ranging between about 40,000 psi and 100,000 psi. Such vessels must therefore be extremely robust to withstand such pressures.

Increasingly, pressure vessels of the type described above are employed for the treatment of products such as food, medical, and biological products. Liquid products, such as beverages, are especially amenable to treatment in pressure vessels, though a wide range of other types of products are also treatable. When a product is placed within a pressure vessel and subjected to such extreme pressures, all living organisms within or on the product are destroyed, effectively sterilizing the product.

The products to be treated are placed in non-rigid containers which are then positioned within the vessel. Remaining space in the vessel is filled by a pressure medium, usually water. The vessel is sealed and subjected to ultra-high pressures, which isostatically press the containers of product. Because of the non-rigid nature of the containers, the containers are able to tolerate the distortion caused by the pressure, due, mostly, to the presence and compression of trapped gasses, such as air bubbles, in the containers.

Frequently, product treatment includes both pressure treatment and temperature treatment. In such cases, it is common to exploit well known adiabatic principles to perform at least a portion of the heat treatment of the product within the pressure vessel. It is well known that temperature, pressure, and volume of a given substance are interrelated. Where the volume is held constant, a rise in pressure will result in a corresponding rise in temperature. If the adiabatic characteristics of a given material are known, a change in temperature can be calculated for a given change in pressure. Thus, in principle it is possible to subject a known product surrounded by a known pressure medium to a selected degree of pressure and predict the temperature that will be reached within the vessel during the pressing process.

However, in practice, several problems may arise. Because different substances have different adiabatic properties, a variety of products placed together within a pressure vessel for pressure treatment can produce thermal gradients within the vessel. Additionally, the vessel, itself, can act as a heat sink, drawing heat from within the vessel. Placement of the product within the vessel and the thermal conduction characteristics of the vessel can affect thermal distribution within the vessel. Under such circumstances, it can be difficult to predict the exact temperature within the vessel, and whether the temperature is consistent throughout. Finally, health codes and regulations that relate to the treatment of food products require that actual temperature measurements be taken during the processing of the food products, to ensure that the product is safely processed. For all of these reasons, it is desirable to have temperature sensors within a pressure vessel while a food product is being treated.

BRIEF SUMMARY OF THE INVENTION

According to an embodiment of the invention, a connector for a pressure vessel is provided, including a connector assembly having a first plurality of contacts, and a receiver assembly configured to be positioned within a receiver aperture formed in a wall of the pressure vessel and having a second plurality of contacts, the receiver assembly being configured to receive the connector assembly and place each of the first plurality of contacts in electrical contact with a corresponding one of the second plurality of contacts. A seal is provided, configured to be positioned between the connector assembly and the wall of the pressure vessel, substantially sealing the receiver aperture from pressure within the vessel.

The connector assembly includes a sensor aperture formed therein and configured to receive a sensor lead from a sensor positioned within the pressure vessel. The connector assembly also includes a sensor lead seal configured to seal the sensor aperture around the sensor lead.

According to another embodiment of the invention, a pressure vessel system is provided, comprising a cylindrical pressure vessel body and first and second closures configured to close respective first and second ends of the pressure vessel body. An aperture is formed in the first closure and a connector receiver assembly is positioned within the aperture.

The system also includes a product carrier sized and configured to be positioned within the pressure vessel, a plurality of sensors configured to be placed within the pressure vessel, and a connector assembly coupled to the product carrier such that when the product carrier is positioned within the pressure vessel, the connector assembly is positioned to make contact with the connector receiver assembly via the aperture formed in the first closure. The connector assembly is configured to receive a lead from each of the plurality of sensors and place the lead in electrical contact with a corresponding contact of the connector receiver assembly.

A seal is coupled to the connector assembly and configured to seal between the aperture in the first closure and the connector assembly, and a spring is positioned and configured to bias the connector assembly against the first closure.

The pressure vessel system further comprises a data acquisition unit configured to receive signals from the plurality of sensors via the connector receiver assembly.

BRIEF DESCRIPTION OF THE SEVERAL VIEWS OF THE DRAWING(S)

DETAILED DESCRIPTION OF THE INVENTION

Figure 1:
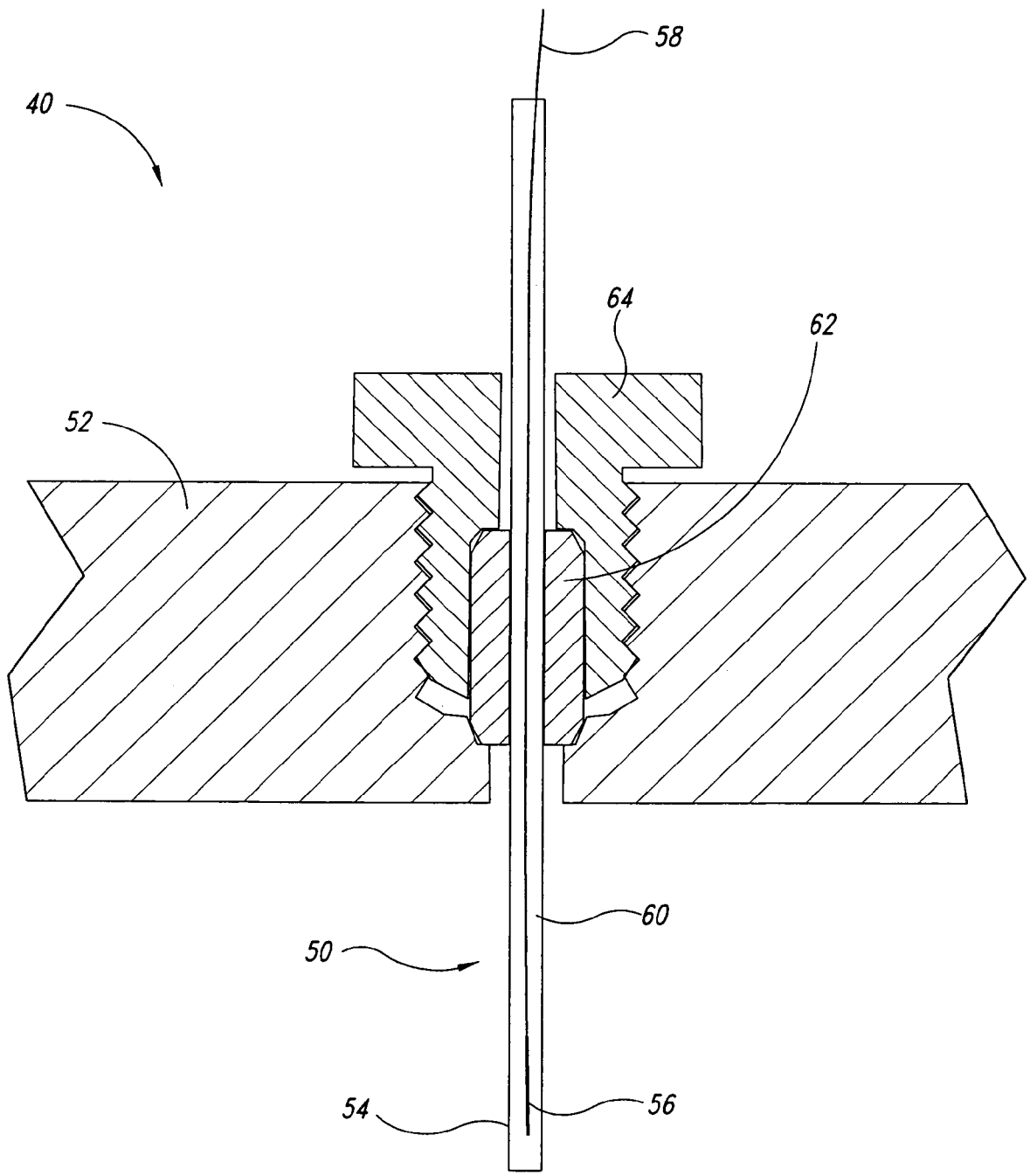
FIG. 1 shows a simplified thermal well sensor according to known art.

A challenge in taking temperature measurements within a pressure vessel is that the monitoring equipment must be capable of withstanding extreme pressures within the pressure vessel. Additionally, temperature measurements must be transmitted to a monitoring device. One known method is the use of thermal wells. FIG. 1 shows a simplified diagram of a thermal well 50. The wall 52 represents either a side wall or a closure of a pressure vessel. The thermal well 50 is cylindrical in shape and extends from the wall 52 into the interior of the pressure vessel. The walls 54 of the thermal well 50 are structured to be capable of withstanding the pressures within the pressure vessel. The interior of the thermal well is maintained at normal ambient pressure. A thermocouple temperature sensing probe (TC) 56 is positioned within the thermal well and surrounded by a thermally conductive material 60. Leads 58 carry temperature data from the TC 56 to a monitoring station. Temperature of a pressure medium within the pressure vessel is transmitted by conduction through the walls 54 of the thermal well 50 to the thermocouple 56. The thermal conduction characteristics of the wall 52 of the pressure vessel and the wall 54 of the thermal well 50 can be known and compensated for. Thus, accurate temperature readings can be obtained by thermal well temperature sensors such as that shown in FIG. 1.

However, such sensors suffer from several disadvantages. First, because of the mass of the walls of the thermal well, as well as the conductive material surrounding the thermocouple, the response time of the sensor device to changes in temperature is slow. Accordingly, brief temperature transients within the pressure vessel cannot be detected by the thermal well sensor.

Second, it can be seen that the thermal well is limited to measuring temperatures near the perimeter of the pressure vessel. Thus, temperatures near the center of the vessel cannot be easily measured during a pressing operation. Finally, the location of a thermal well is fixed. As a result, an operator cannot select specific sites for temperature monitoring.

Ideally, disconnectable and repositionable temperature probes would be of great use in monitoring temperature within a pressure vessel. This would require, however, the use of electrical connectors within the pressure vessel. A difficulty is that conventional electrical connectors cannot withstand the extreme pressures. In a vessel employing water as a pressure medium, the water will eventually come into contact with the contact surfaces of the connector. Under high pressure, the conductive characteristics of water undergo changes, and even highly purified water becomes conductive, interfering with the signals from the probes and eventually shorting the probes completely.

Figure 2A:
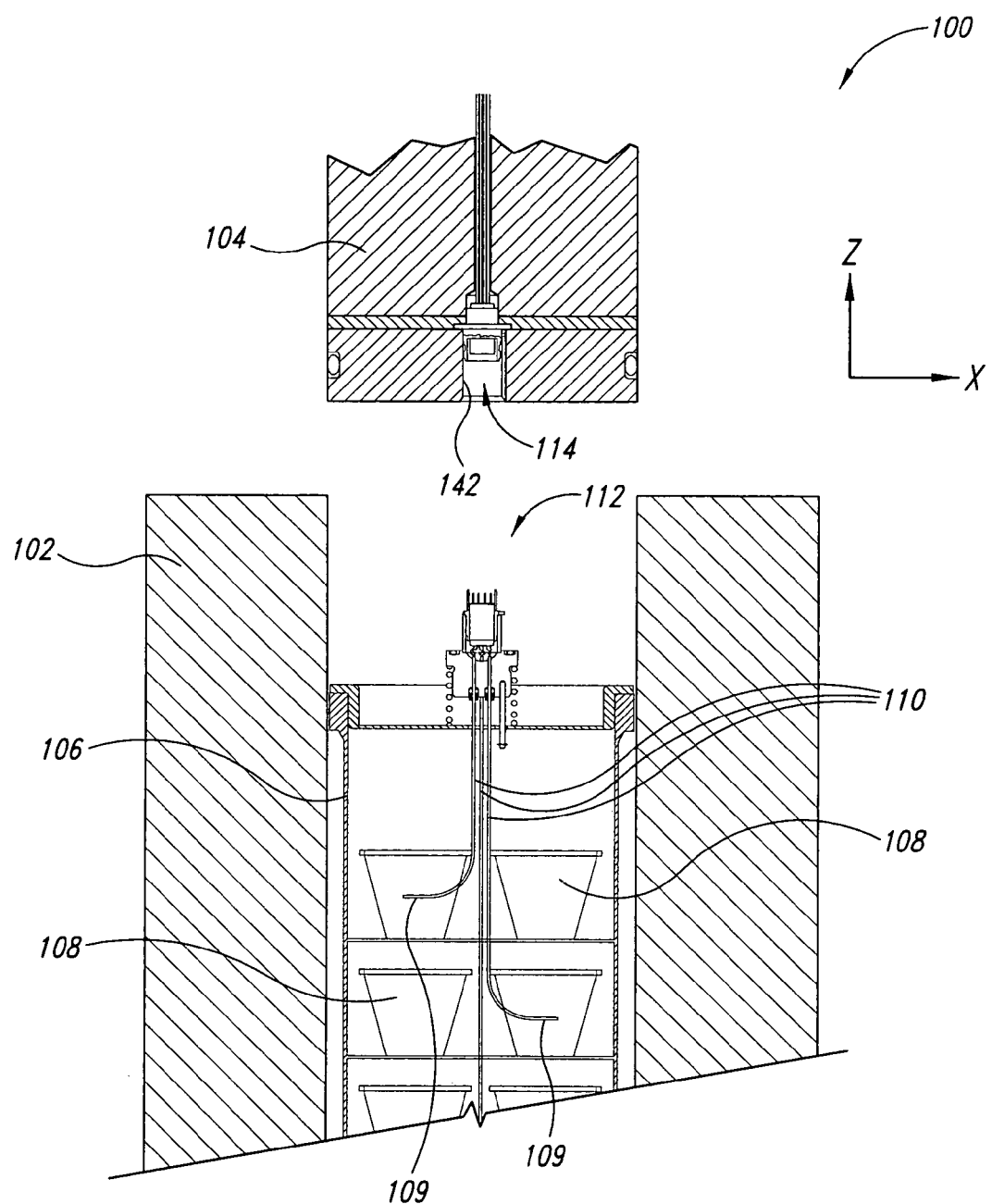
FIGS. 2A and 2B show a pressure vessel with a sensor connector system according to an embodiment of the invention.
Figure 2B:
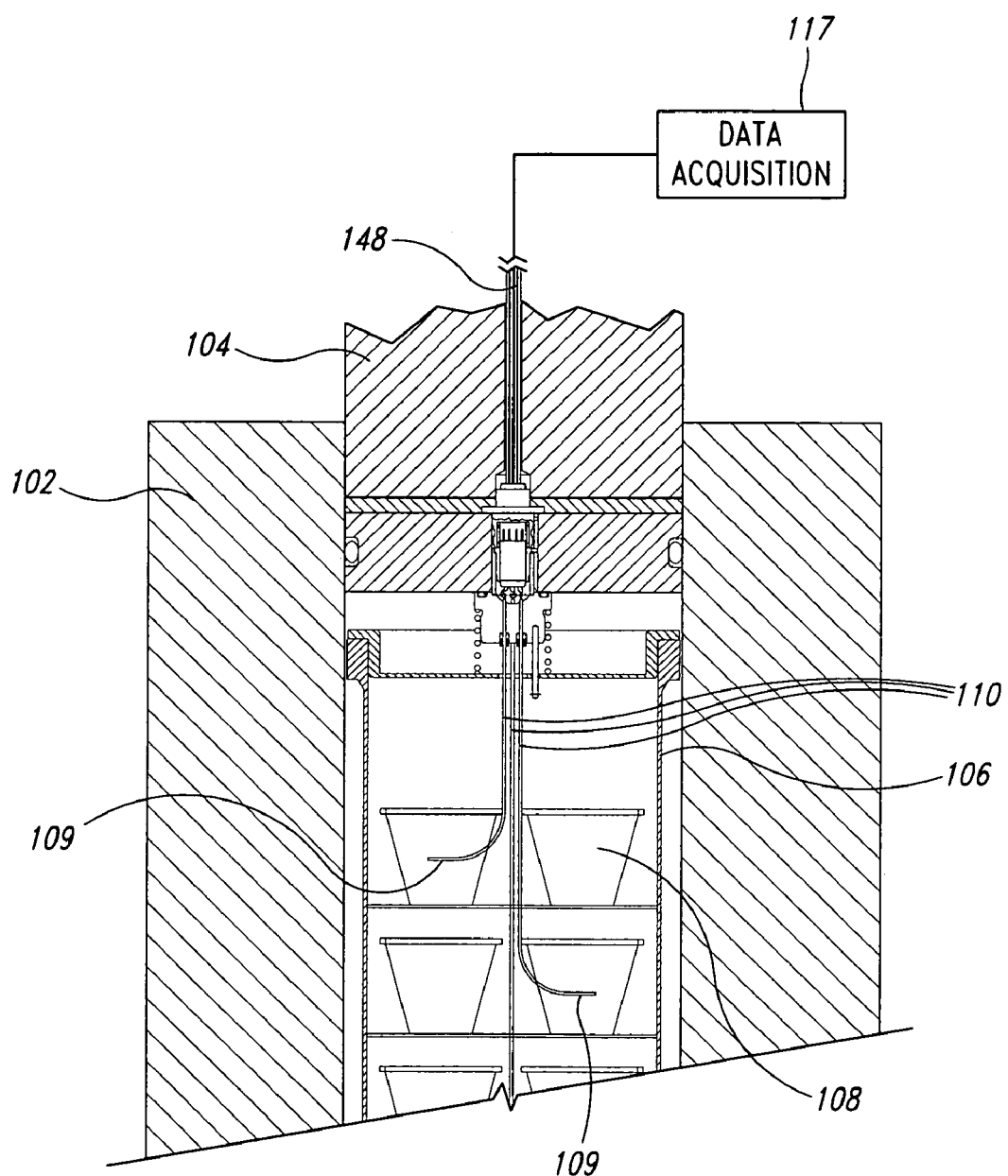

FIGS. 2A and 2B show a vertical cross section of a pressure vessel 100 incorporating a temperature monitoring system according to an embodiment of the invention. FIG. 2A includes a reference key indicating the x and z axes, while the y axis is perpendicular to the plane of the figure.

The pressure vessel 100 includes a body 102 and an upper closure assembly 104. Though not shown, the vessel 100 also includes a lower closure assembly. Components of the upper and lower closure assemblies will not be described in detail, and, for brevity, a closure assembly may simply be referred to as a closure.

A product carrier 106 is positioned within the pressure vessel 100 and is shown with a number of product containers 108 positioned on the carrier 106 for pressure treatment within the vessel 100. Thermocouple temperature probes 109, such as are well known in the art, are positioned at locations selected to monitor temperatures immediately adjacent to the product containers 108. Leads 110 from each of the thermocouple probes 109 terminate at a connector assembly 112 that is coupled to the product carrier 106. The closure 104 includes a connector receiver assembly 114 positioned within an aperture 142 provided in the closure 104 for this purpose.

FIG. 2A shows the pressure vessel 100 with the closure assembly 104 separated from the body 102. As will be described in more detail below, the connector receiver assembly 114, which may also be referred to as the receiver assembly, is located in a position that corresponds in the x and y axes to the position of the connector assembly 112. For example, the connector assembly 112 and the connector receiver assembly 114 may each be positioned at the longitudinal axis of the cylindrical pressure vessel 100. When the closure 104 is lowered into the opening of the vessel body 102, the connector assembly 112 is received into the connector receiver assembly 114, and pins in electrical communication with the individual traces of the thermocouple probes 109 are received into a socket of the connector receiver assembly 114, where they are placed in electrical communication with a data acquisition unit 117 via signal leads 148.

The data acquisition unit 117 may be any device adapted to receive signals from the thermocouple probes 109, such as a dedicated module, a portion of a controller for the pressure vessel 100, a computer, or any other appropriate device, and may include a memory for storing data, a processing unit for comparing or otherwise manipulating data from the probes 109, a video monitor for displaying information related to the acquired data, etc.

Figure 3A:
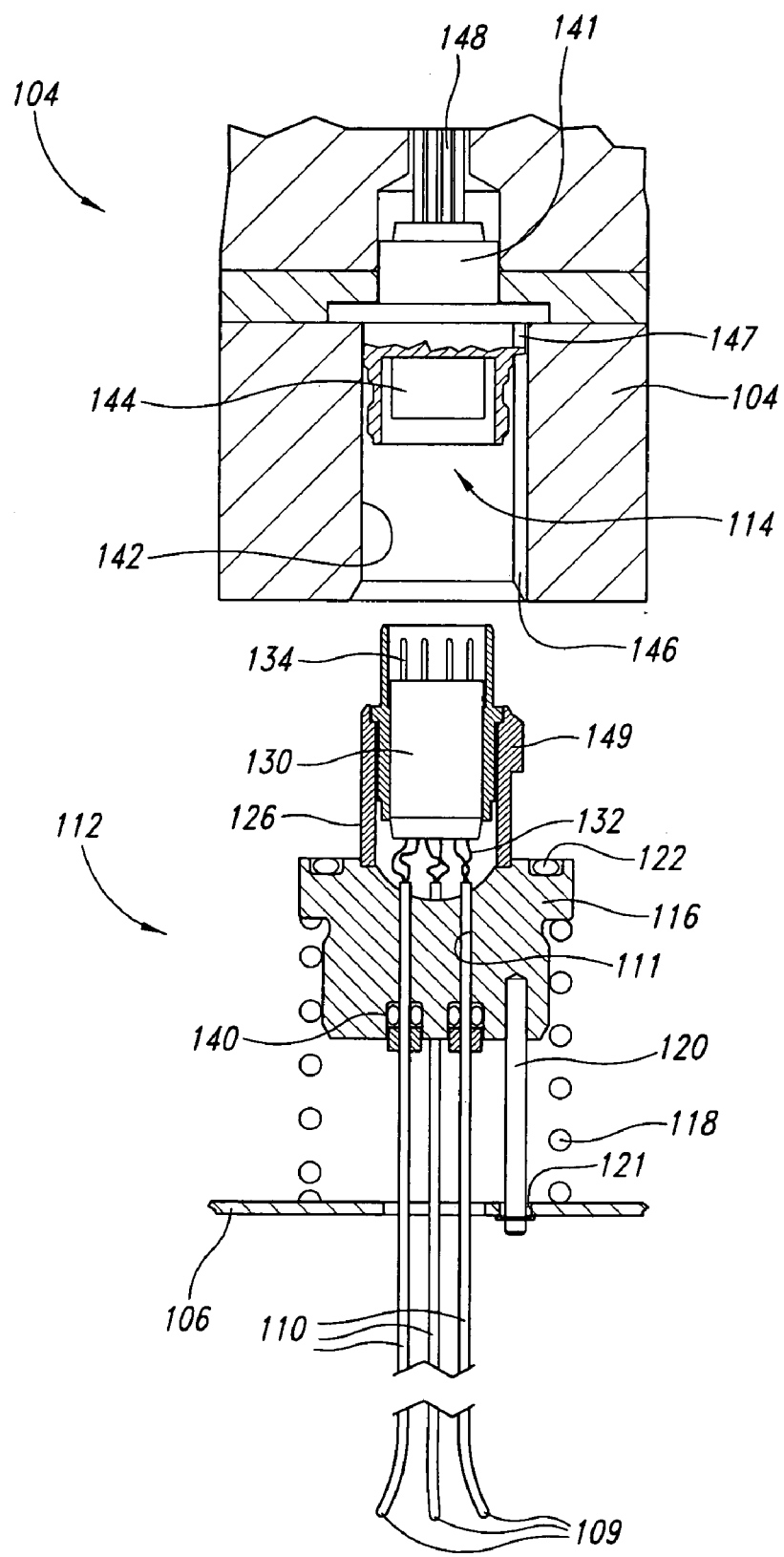
FIGS. 3A-3C show, in greater detail and at various stages, the connector portion of the pressure vessel of FIGS. 2A and 2B.
Figure 3B:
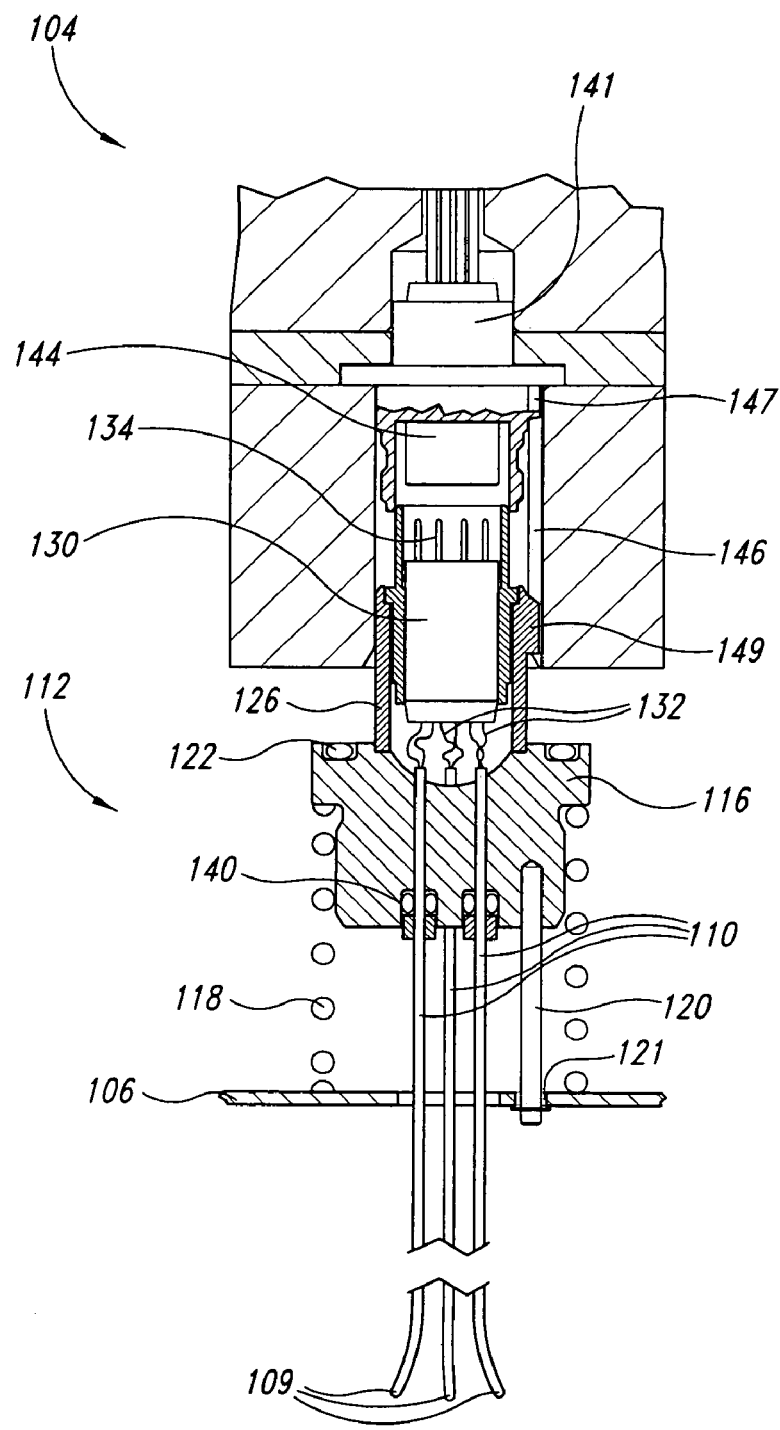
Figure 3C:
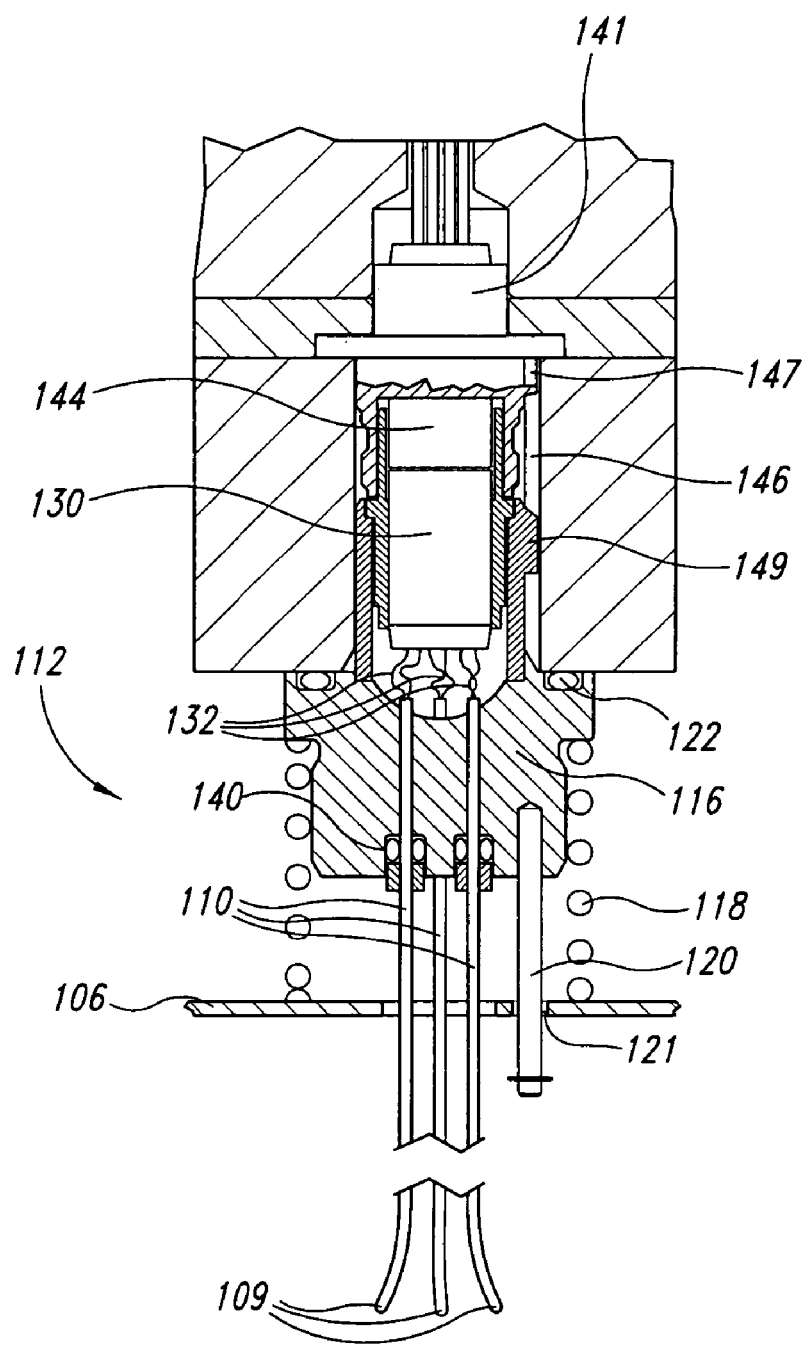

Referring now to FIGS. 3A through 3C, detailed views of the connector assembly 112 and the connector receiver assembly 114 are shown in various relative positions.

The connector assembly 112 includes a cap 116, an extension 126, and a plug 130. The cap 116 is coupled to the carrier 106 via a spring 118. An alignment guide 120 extends from the cap 116 downward toward the carrier 106, where it passes through an aperture 121 in the carrier 106, thereby providing a rotational index for the connector assembly 112 relative to the carrier 106. Leads 110 of the thermocouple probes 109 pass through corresponding apertures 140 in the cap 116. The extension 126 extends upward from the cap 116 and is configured to receive the plug 130 therein. The plug 130 includes a plurality of connector pins 134, each in electrical communication with a corresponding trace 132 of one of the thermocouple probes 109. An indexing feature (not shown) of the plug 130 allows correct rotational alignment of the plug 130 with the extension 126. The connector assembly 112 further includes pressure activated seals 140 positioned and configured to seal a space between the leads 110 of respective thermocouple probes 109 and the apertures 111 through which the leads 110 pass to communicate with the plug 130. A seal 122 is positioned in a corresponding feature of the cap 116, as shown.

The closure assembly 104 includes an aperture 142 penetrating through the closure 104. The connector receiver assembly 114 includes a socket carrier 141 positioned within the aperture 142 and a socket 144 positioned within the socket carrier 141. The socket 144 comprises a plurality of contact apertures (not shown) corresponding in position to respective ones of the plurality of connector pins 134, such that, when the socket 144 is engaged by the plug 130, each of the connector pins 134 is received by the corresponding one of the contact apertures. Each of the contact apertures is in turn in electrical contact with a corresponding signal lead 148. Sockets and plugs similar to those described herein are well known in the art. Accordingly, neither the socket 144 nor the plug 130 are described or shown in detailed cross section. The socket carrier 141 is also not shown in full cross section, though a portion thereof is shown cutaway to reveal the socket 144.

The aperture 142 includes an indexing groove 146, which is engaged by an index tab 147 of the socket carrier 141, thereby providing correct rotational alignment for the socket 144, relative to the closure assembly 104.

In operation, product to be pressure treated is positioned on the product carrier 106. The thermocouple probes 109 are positioned at selected locations around the carrier 106. The selection of these locations may be in accordance with any appropriate criteria. For example, it may be desirable to record a temperature gradient between a central region of the pressure vessel and a region near a side wall thereof. Accordingly, a first thermocouple 109 would be positioned centrally in the product carrier 106 and a second thermocouple 109 would be positioned near a perimeter of the product carrier 106. Alternatively, it may be desirable to collect temperature readings at various points close to selected ones of the product containers 108 (see FIGS. 2A and 2B). Accordingly, thermocouples 109 would be appropriately positioned for this purpose.

Once the product has been placed on the product carrier 106, and the thermocouples 109 have been appropriately positioned, the product carrier 106 is lowered into the pressure vessel 100. As the product carrier 106 is lowered into the pressure vessel 100, indexing features on the product carrier 106 engage corresponding features on the interior of the pressure vessel 100. Such indexing features may include, for example, shallow apertures formed on a bottom closure of the pressure vessel, positioned to receive support legs of the product carrier 106 and provide positive rotational positioning for the carrier. Alternatively, one or more grooves or ridges may be formed along inner walls of the body 102, which are then engaged by corresponding features of the product carrier 106. Other acceptable indexing systems are within the ability of one having ordinary skill in the art, and so will not be discussed in detail.

Water is a common pressure medium for pressure treatment of food and medical products. The pressure vessel 100 may have water provided therein prior to the placement of the product carrier 106, in which case, the product carrier is lowered into the water within the pressure vessel 100.

Once the product carrier 106 is properly positioned within the pressure vessel, the closure assembly 104 is positioned above and aligned coaxially with the vessel body 102, as shown in FIG. 2A and, in more detail, in FIG. 3A. The closure assembly 104 is positioned rotationally in accordance with appropriate indices (not shown), and lowered into the vessel body 102. Because the product carrier 106 and the closure assembly 104 are rotationally aligned with corresponding indices of the pressure vessel body 102, and because the cap 116 is maintained in rotational alignment with the product carrier 106 by the alignment guide 120, the connector assembly 112 is substantially aligned with the receiver assembly 114.

As may be seen in FIG. 3B, an index tab 149 of the extension 126 engages the indexing groove 146 on the interior of the aperture 142 as the closure assembly 104 is lowered. This engagement further refines the rotational alignment of the connector assembly 112 and the receiver assembly 114. Finally, the connector pins 134 of the plug 130 engage the corresponding contact apertures of the socket 144, and firm electrical contact is established between each of the thermocouples 109 and the data acquisition unit 117.

As the closure assembly 104 lowers to its final position, as shown in FIG. 3C, the spring 118 compresses, biasing the connector assembly 112 against the closure assembly 104 and ensuring firm contact between the connector pins 134 and the respective apertures, and between the seal 122 and the lower surface of the closure assembly 104.

When the closure 104 is properly positioned in the vessel body 102, and the vessel is filled with pressure medium, the system is pressurized to a selected pressure. As the pressure within the vessel rises, the seal 122 between the cap 116 and the lower surface of the closure assembly 104 is driven by the pressure to seal the joint between the cap and the closure 104. In a like manner, the seals 140 around each of the thermocouple probes, where they pass into the apertures 111 of the cap 116, are driven to seal the respective apertures 111. The seals 122 and 140 prevent the passage of pressure medium into the aperture 146, and the pressure in the aperture remains at ambient pressure.

The particular indexing means described above for indexing the various components of the system are described merely as examples. Alternative means for indexing the connector assembly 112 with the aperture 142, for example, are within the abilities of one of ordinary skill. For example, the respective shapes of the extension 126 and the aperture 142 may be selected such that, as the closure assembly is lowered, the connector assembly 112 can be rotated from several degrees out of position to correctly align with the connector receiver assembly 114. Such modifications are within the abilities of one having ordinary skill in the art.

As a safety feature, the spring 118 is provided with sufficient additional travel that, in the event the pins 134 fail to engage the corresponding contact apertures, the plug 130 will not be forced, by the lowering of the closure assembly, to fully engage the socket 144, which would damage the plug 130, the socket 144, or both. Instead, the cap 116 will be pressed further down as the spring 118 compresses further. If a full connection is not made, the acquisition unit 117 may be configured to detect the failed connection, prevent the pressurizing of the vessel 100, and signal a connection error.

As another safety feature, a pair of open leads may be provided in the receiver assembly 114. This may simply be a pair of contact apertures in the socket 144 for which there are no corresponding connector pins 134. The data acquisition unit 117 may be configured to monitor conduction between the open leads, and signal a seal failure if a change in conduction is detected. In the event that a seal associated with the connector assembly 112 fails, pressure medium will be forced into the aperture 142 and will make contact with the open leads, changing the conduction characteristics between them and provoking a detection response from the acquisition unit 117.

It may be seen that embodiments of the invention provide significant advantages during a pressurization process. For example, accurate and responsive temperature readings can be conducted during the process. The locations of the probes can be selected according to requirements that may vary with different pressurizing operations. At a more basic level, embodiments of the invention make it possible to provide an electrical connection inside a pressure vessel, which can be disconnected and reconnected.

Another advantage afforded by embodiments of the invention is that, because temperature sensing probes are positioned on or in the product carrier, rather than the vessel itself, they may be transported with the carrier to other process steps. In some product treatment processes, the product is subjected to a heat processing step outside the pressure vessel, in addition to the heating that occurs within the vessel. This is generally performed prior to the pressurizing step, and may involve immersing the carrier, loaded with the product, into a heated fluid bath.

According to an embodiment of the invention, the connector assembly on the carrier is connected to a connector receiver assembly provided at the fluid bath to permit monitoring of the fluid temperature immediately adjacent to the food product during the process step. Following the fluid bath, the carrier is transported to the pressure vessel and processed as described above. It is therefore possible, in accordance with the present invention, to provide means for accurately and consistently monitoring the temperature of a product through any number of heating and/or chilling steps in a process without the need to emplace different sensors for different steps in the process.

Another advantage afforded by embodiments of the invention, is that, through an understanding of the adiabatic properties of the material being processed, an exact drop in temperature can be predicted, when the pressure in the vessel is released, based on the measured temperature under pressure. Thus, a confirmation of the pressure step can be made by comparing the predicted temperature drop with the measured temperature drop.

Figure 4:
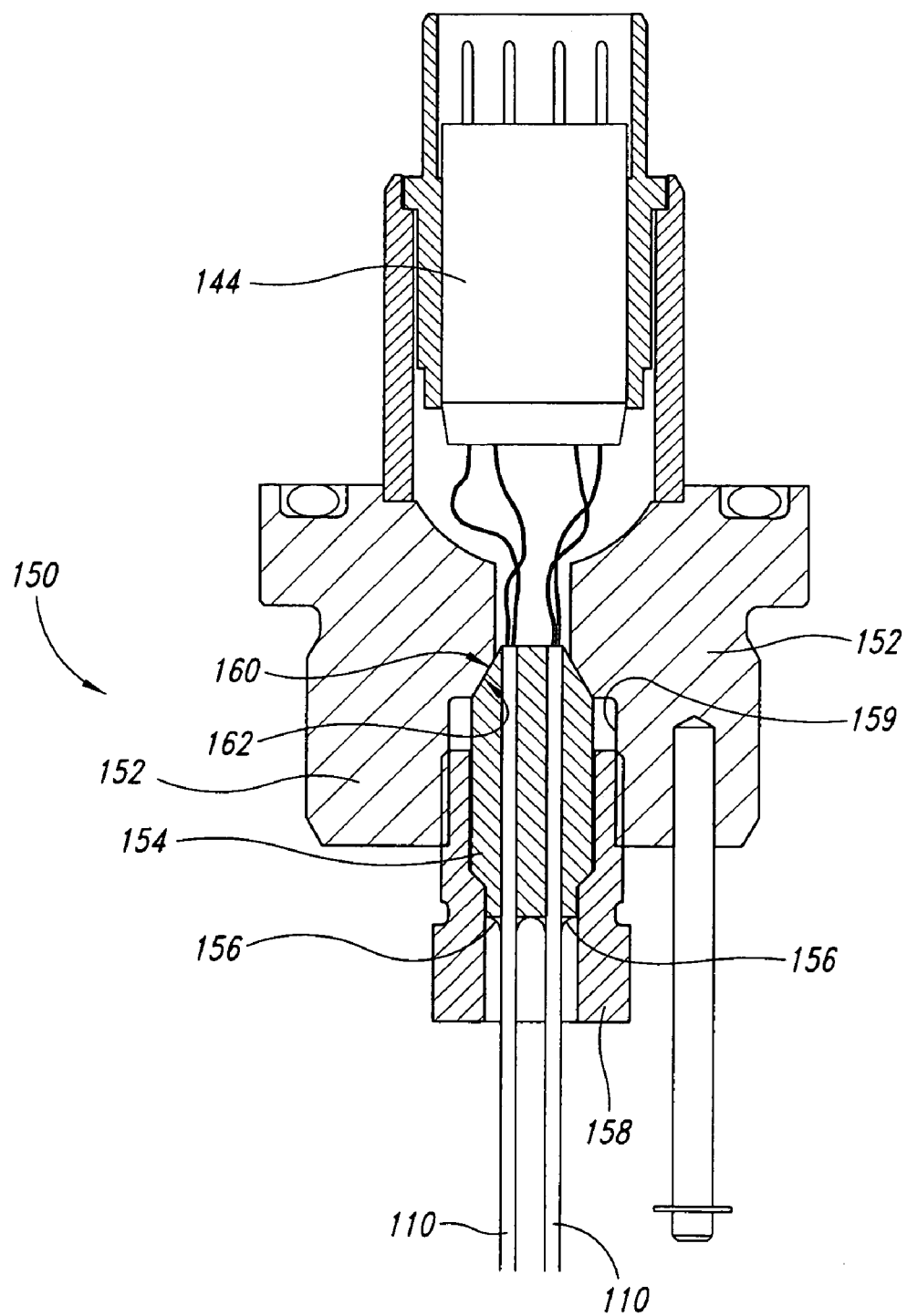
FIG. 4 shows a connector assembly according to an alternate embodiment of the invention.

Referring now to FIG. 4, a connector assembly 150 according to an alternate embodiment of the invention is illustrated. According to the embodiment of FIG. 4, the leads 110 are coupled to a cap 152 via apertures formed in a compression fitting 154. The metallic sheathing of the leads 110 is brazed to the compression fitting 154 at brazed joints 156, forming a dependable seal. The dimensions and composition of the brazed joints 156 are selected to be capable of tolerating the pressure within the pressure vessel. The compression fitting 154 includes a frusto-conical sealing surface 160 that is received by a corresponding frusto-conical seat 162. A compression nut 158 engages an outer surface of the fitting 154 and threads into a corresponding aperture 159 formed in the cap 152, biasing the sealing surface 160 against the seat 162 to establish a reliable seal.

A more detailed discussion of compression joints in general may be found in U.S. patent application Ser. No. 10/922,030, incorporated herein in its entirety by reference.

Figure 5:
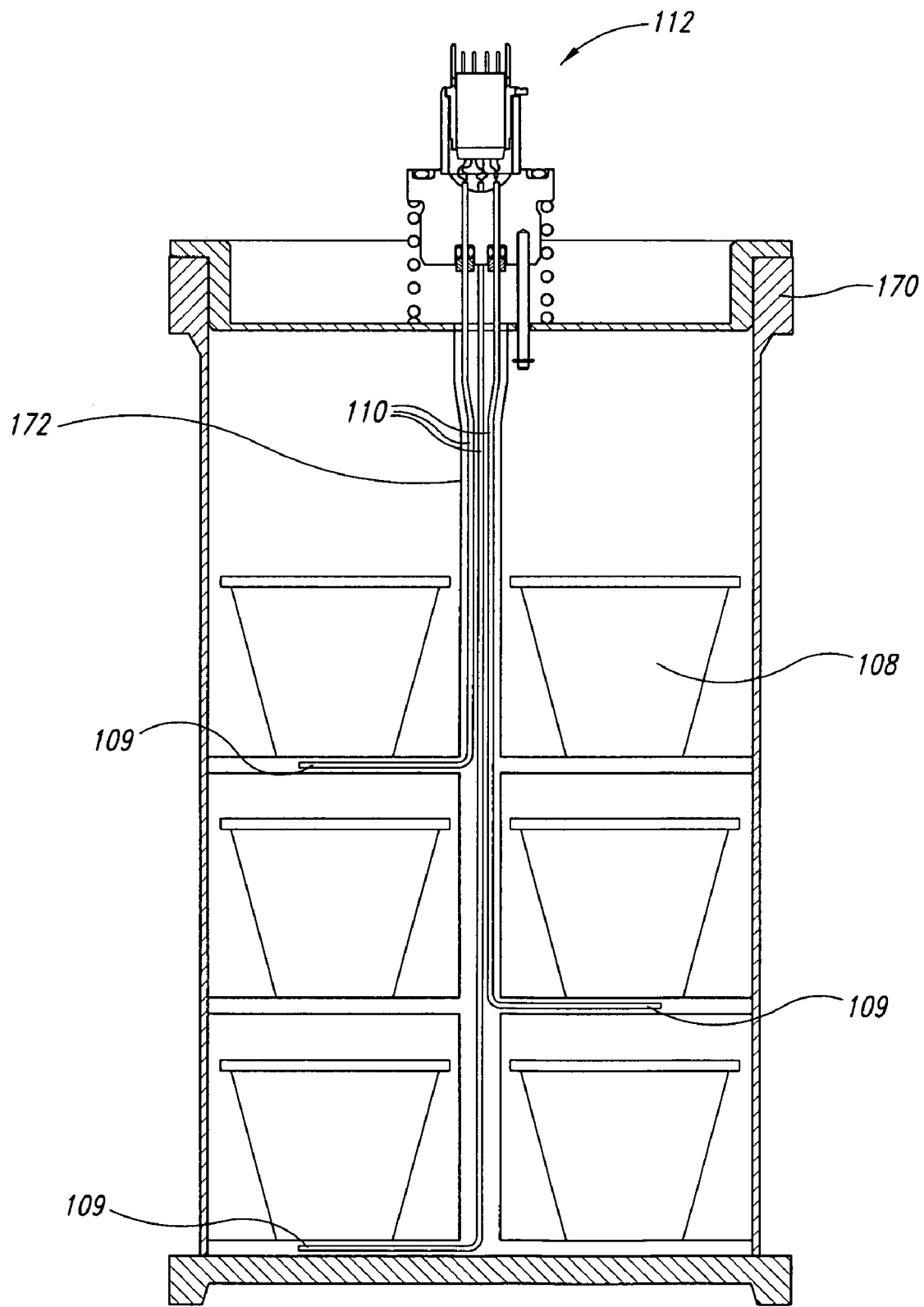
FIG. 5 shows a product carrier according to an alternate embodiment of the invention.

FIG. 5 illustrates a product carrier 170 according to another embodiment of the invention. The carrier 170 includes a conduit 172 through which the thermocouple probe leads 110 pass. Probes 109 are positioned in or under support shelves of the product carrier.

For particular types of processes, the embodiment of FIG. 5 offers some possible advantages over the product carrier 106 of FIGS. 2A and 2B. As described above with reference to FIGS. 2A and 2B, the probes 109 of the product carrier 106 are positioned during or after the carrier 106 is loaded with product. This arrangement is useful when the type of product being treated varies, or when different measurements are to be taken with succeeding pressure cycles, as when a series of tests is underway. In such situations, it may be desirable to frequently change the location of the probes. However, when a production run is undertaken, in which the product carrier is to be repeatedly reloaded with a same type of product, and undergo a same heat and pressure treatment, placing temperature probes manually with each new load of the product carrier is a time consuming part of the process.

By pre-positioning the probes 109 on the carrier 170 at predetermined positions, and unloading and reloading the carrier 170 without the need to reposition the probes 109, process speeds can be increased and cycle times reduced. At the same time, consistent and reliable temperature measurements can be taken over a series of cycles, which permits more accurate control of the process and quality, and better predictability of results.

Embodiments have been described in which the connector assembly is provided at the top of the product carrier. It will be recognized that, in a similar manner, a connector assembly may be provided on a bottom portion of the product carrier, configured to engage a connector receiver assembly positioned in a bottom closure assembly of the pressure vessel as the carrier is lowered into the vessel.

In another alternate embodiment, the connector receiver assembly is provided in an aperture formed in a wall of the vessel body, and the connector assembly is positioned by hand in the aperture after the carrier is placed in the vessel. While this arrangement involves additional handling, as compared to other embodiments, some product carrier configurations may necessitate such an arrangement.

For the purposes of the claims, unless specifically limited to the wall of the vessel body, a claim reciting a wall of a pressure vessel is considered to read on the closure of the vessel and the body thereof.

The actual configuration of the carrier is a design choice dictated by various issues including capacity of the associated pressure vessel, type of product to be processed, other process steps in which the product may remain on the carrier, cost of manufacture and assembly, type and location of sensors, etc.

The sensors need not necessarily be thermocouples, but may be of any appropriate type, and may further be configured to monitor other parameters within the pressure vessel, such as pressure, or parameters that may be of interest in other process steps, such as acceleration, light, etc.

Provided the devices can tolerate the conditions of the pressure vessel, any type of active or passive device may be incorporated into the product carrier and provided with control or monitor connections via the connector assembly. Usefulness of these devices may be limited to other process steps, but by integrating them with the carrier, they can be accessed during those other process steps simply by providing a connector receiver assembly for that purpose.

Design considerations such as those described above are within the abilities of one having ordinary skill in the art, and are considered to fall within the scope of the invention.

Embodiments of the invention have been described in association with a combination heat/pressure process in which the heat is achieved through enthalpy, alone. In some processes, additional heat may be provided by heating the pressure medium as it is placed in the vessel, for example, or by providing heating means within the vessel.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A pressure vessel system, comprising:
   a pressure vessel body;
   first and second closures configured to close respective first and second ends of the pressure vessel body;
   an aperture formed in the first closure;

a connector receiver assembly positioned within the aperture;

a product carrier sized and configured to be positioned within the pressure vessel;

a plurality of sensors configured to be placed within the pressure vessel; and a connector assembly coupled to the product carrier such that when the product carrier is positioned within the pressure vessel, the connector assembly is positioned to make contact with the connector receiver assembly via the aperture formed in the first closure, the connector assembly being configured to receive a lead from each of the plurality of sensors and place the lead in electrical contact with a corresponding contact of the connector receiver assembly.

2. The system of claim 1, further comprising a seal coupled to the connector assembly and configured to seal between the aperture in the first closure and the connector assembly.

3. The system of claim 1, further comprising a spring configured to bias the connector assembly against the first closure.

4. The system of claim 1, further comprising a data acquisition unit configured to receive signals from the plurality of sensors via the connector receiver assembly.

5. The system of claim 1, further comprising indexing means for rotationally aligning the connector assembly with the connector receiver assembly.

6. The system of claim 1 wherein the first closure is an upper closure of the pressure vessel, and wherein the connector assembly is coupled to the product carrier such that when the product carrier is positioned within the pressure vessel and the first closure is lowered toward a closed position relative to the pressure vessel body, the connector assembly makes contact with the connector receiver assembly via the aperture formed in the first closure.

* * * * *